(12) United States Patent
Powell et al.

(10) Patent No.: US 10,470,914 B2
(45) Date of Patent: Nov. 12, 2019

(54) METHOD AND APPARATUS FOR CORRECTING FOOT AND ANKLE PROBLEMS AND PROBLEMS WITH GAIT

(71) Applicant: MD Orthopaedics, Inc., Wayland, IA (US)

(72) Inventors: Marcus William Powell, New London, IA (US); John R Mitchell, Danville, IA (US)

(*) Notice: Subject to any disclaimer, the term of this patent is extended or adjusted under 35 U.S.C. 154(b) by 0 days.

(21) Appl. No.: 15/965,138

(22) Filed: Apr. 27, 2018

(65) Prior Publication Data

US 2018/0311065 A1 Nov. 1, 2018

Related U.S. Application Data

(60) Provisional application No. 62/490,690, filed on Apr. 27, 2017, provisional application No. 62/629,424, filed on Feb. 12, 2018.

(51) Int. Cl.
*A61F 5/01* (2006.01)

(52) U.S. Cl.
CPC ............ *A61F 5/0127* (2013.01); *A61F 5/013* (2013.01); *A61F 5/0125* (2013.01); *A61F 5/0116* (2013.01); *A61F 2005/0167* (2013.01); *A61F 2005/0169* (2013.01); *A61F 2005/0179* (2013.01)

(58) Field of Classification Search
CPC ............ A61F 5/0125; A61F 2005/0167; A61F 5/0102; A61F 5/0103; A61F 5/0127; A61F 2005/0165; A61F 5/0116; A61F 2005/0134; A61F 2005/0137; A61F 2005/0141; A61F 2005/0179; A61H 1/024; A61H 1/0277
USPC .................................. 602/5, 23, 26, 27, 16
See application file for complete search history.

(56) References Cited

U.S. PATENT DOCUMENTS

| | | |
|---|---|---|
| 2,585,342 A | 2/1952 | Morgan |
| 2,906,261 A | 9/1959 | Craig |
| 3,171,407 A | 3/1965 | Rogers |
| 3,523,526 A | 8/1970 | Phelps |
| 3,777,747 A | 12/1973 | Friedman |
| 3,892,231 A | 7/1975 | Tummillo |
| 4,088,129 A | 5/1978 | DiGiulio |
| 4,495,943 A | 1/1985 | Kurtz et al. |
| 5,346,463 A | 9/1994 | Devens |
| 5,382,225 A | 1/1995 | Sutcliffe |
| 5,401,235 A | 3/1995 | Devens |

(Continued)

OTHER PUBLICATIONS

Ponseti_global_clubfoot_initiative.PDF (published online: Aug. 16, 2015) (Year: 2015).*

(Continued)

*Primary Examiner* — Ophelia A Hawthorne
*Assistant Examiner* — Caitlin A Carreiro
(74) *Attorney, Agent, or Firm* — Nyemaster Goode, P.C.

(57) ABSTRACT

An AFO for use in the Ponseti method which is bar-less and provides for readily interchangeable structures for providing differing articulation resistance. In one embodiment, the readily interchangeable structure is a flexible member achieving connection between and the majority of the separation between the shoe and the calf engaging structure. In another embodiment, an articulated arm with two rigid segments joined at a spring loaded hinge, with interchangeable spring canisters is used.

11 Claims, 15 Drawing Sheets

(56) References Cited

U.S. PATENT DOCUMENTS

| | | | |
|---|---|---|---|
| 5,470,310 A * | 11/1995 | Sutcliffe | A61F 5/0193 128/882 |
| 5,483,757 A | 1/1996 | Frykberg | |
| 5,489,258 A | 2/1996 | Wohnsen et al. | |
| 5,575,764 A * | 11/1996 | Van Dyne | A61F 5/0125 482/124 |
| 5,997,493 A * | 12/1999 | Young | A61F 5/0125 602/16 |
| 6,173,511 B1 | 1/2001 | Perrault | |
| 6,328,707 B1 | 12/2001 | Lampkins | |
| 6,500,138 B1 * | 12/2002 | Irby | A61F 5/0125 602/26 |
| 7,270,644 B2 | 9/2007 | Ingimundarson | |
| 7,364,557 B2 * | 4/2008 | Yumikino | A61F 5/0125 602/16 |
| 7,438,698 B2 | 10/2008 | Daiju | |
| 7,513,880 B2 | 4/2009 | Ingimundarson et al. | |
| 7,569,023 B2 | 8/2009 | Dobbs | |
| 7,584,556 B2 | 9/2009 | Fujita et al. | |
| 7,645,251 B2 | 1/2010 | Hatton et al. | |
| 7,867,184 B2 | 1/2011 | Mitchell | |
| 7,922,677 B2 | 4/2011 | Daiju | |
| 7,988,652 B2 * | 8/2011 | Chao | A61F 5/0125 128/868 |
| 8,005,651 B2 | 8/2011 | Summit et al. | |
| 8,083,703 B2 | 12/2011 | Daizade | |
| 8,417,487 B2 | 4/2013 | Summit et al. | |
| 8,613,716 B2 | 12/2013 | Summit et al. | |
| D704,845 S | 5/2014 | Daizade | |
| D704,846 S | 5/2014 | Daizade | |
| 8,771,213 B2 | 7/2014 | Wens | |
| 8,777,884 B2 | 7/2014 | DeHeer et al. | |
| 8,852,233 B2 | 10/2014 | Burke | |
| 8,986,234 B2 | 3/2015 | Summit et al. | |
| 9,314,391 B2 | 4/2016 | Pittaccio et al. | |
| 9,375,342 B2 | 6/2016 | DeHeer et al. | |
| 2004/0068215 A1 * | 4/2004 | Adelson | A61F 5/0123 602/26 |
| 2010/0010409 A1 * | 1/2010 | Bejarano | A61F 5/0125 602/16 |
| 2010/0160844 A1 * | 6/2010 | Gilbert | A61F 2/64 602/16 |
| 2013/0226059 A1 * | 8/2013 | Morris | A61F 5/0111 602/27 |
| 2016/0374844 A1 * | 12/2016 | DeHarde | F16F 15/04 602/16 |

OTHER PUBLICATIONS

Section from p. 454 of the Atlas of Orthoses and Assistive Devices by Hsu, Michael and Fisk; American Academy of Orthopaedic Surgeons.

* cited by examiner

METHOD AND APPARATUS FOR CORRECTING FOOT AND ANKLE PROBLEMS AND PROBLEMS WITH GAIT

CROSS REFERENCE TO RELATED APPLICATIONS

This application claims the benefit of provisional application filed on Apr. 27, 2017 and having Ser. No. 62/490,690; by the same inventors, and provisional application filed on Feb. 12, 2018 and having Ser. No. 62/629,424 having the same inventors, both of which are hereby incorporated herein in their entirety by these references.

BACKGROUND OF THE INVENTION

The present invention generally relates to the Ponseti method (also known as the Ponseti technique), a nonsurgical technique that uses a series of casts, followed by an abduction brace, or ankle foot orthosis (AFO), to correct congenital clubfoot. The condition causes a baby's feet to turn inward and downward; if not corrected, the child will be unable to walk or move properly. Page 454 of the Atlas of Orthoses and Assistive Devices by Hsu, Michael and Fisk; American Academy of Orthopaedic Surgeons includes the following section.

Various orthoses are used for treatment of clubfoot. Most often, the orthosis is used as a holding device after correction by nonoperative or surgical methods. Typically a more restrictive orthosis is used initially on a full-time schedule. Once the child begins to crawl and/or walk, different bracing regimens for daytime and sleeping can be prescribed.

Scarpa in 1803 gave the first detailed description of an orthosis for treatment of clubfoot. The device was an AFO with metal upright bars and cuffs at the proximal calf and the malleoli, with a cup gripping the hindfoot. The orthosis produced a pronation and an abduction moment at the forefoot.

The Denis Browne bar, also known as the Denis Browne splint or foot abduction orthosis, is a medical device which, and/or variations of it, have been successfully used for decades as part of the Ponseti method. In 1934, Denis Browne described a treatment which included taping the feet onto a bar to maintain the position obtained by manipulation. Modern variations include the Ponseti® abduction bar commercially available from www.mdorthopaedics.easyordershop.com.

In US Patent Application Publication US 2013/0226059 A1, inventor Phillip Morris describes an AFO which is independently worn on a foot and leg of a patient without a connection to a Denis Browne bar connecting the feet. This "bar-less" brace was configured with two spring loaded joints to permit movement while urging the foot to return to a predetermined therapeutic orientation. A Morris AFO could be used on one or both feet.

While the Morris AFO is enjoying some success, it has a drawback in that the springs which provide the biasing forces to urge return of the foot to the therapeutic orientation may need to be adjusted, replaced or exchanged, which can require a considerable amount of strength, degree of skill and labor.

Consequently, there exists a need for AFOs which, among other things, avoid the need for springs or at least some of the skill, strength and time required for making changes to the spring.

SUMMARY OF THE INVENTION

It is an object of the present invention to provide an orthosis without the need for a time consuming process, by highly skilled and strong workers, for spring adjustment/replacement.

It is a feature of the present invention to provide an orthosis without two rigid articulated arms each coupled to a spring for providing biasing forces urging return to a therapeutic orientation.

It is an advantage of the present invention to eliminate the need for highly capable persons to be involved with changes to the springs.

It is another feature of the present invention to include a flexible brace.

It is another advantage to entirely avoid the use of springs.

It is yet another feature of the present invention to utilize an orthosis with an interchangeable spring cartridge.

It is yet another advantage to permit rapid adjustment/replacement of a spring, by persons without extraordinary mechanical skills and strength.

The present invention is a method of reconfiguring a tensioner in an orthosis on an extremity joint comprising the steps of:

providing a first extremity engaging structure configured to be disposed on an extremity and immediately above a joint on the extremity;

providing a second extremity engaging structure configured to be disposed on the extremity and immediately below the joint;

providing an articulated structure coupled to said first extremity engaging structure and said second extremity engaging structure;

said articulated structure being configured with a variable resistance mechanism for resisting relative movement between said first extremity engaging structure and said second extremity engaging structure;

removing from said articulated structure, a first canister having a first predetermined resistance characteristic and a first predetermined exterior shape and size characteristic;

determining that said first predetermined resistance characteristic is one of excessive resistance and insufficient resistance;

locating a second canister having a second predetermined resistance characteristic and second exterior shape and size characteristic;

wherein said second predetermined resistance characteristic is a lower resistance characteristic when a result of said step of determining that said first predetermined resistance characteristic is excessive resistance and is a higher resistance characteristic when said result of said step of determining that said first predetermined resistance characteristic is insufficient resistance; and inserting said second canister in a void vacated by removing said first canister.

Additionally, the present invention is an apparatus for treating clubfoot comprising: an ankle foot orthosis for use in performing a method for treating clubfoot, known as Ponseti method; the orthosis comprising, in operative combination:

a first extremity engaging structure configured to be disposed on an extremity and immediately above a joint on the extremity;

a second extremity engaging structure configured to be disposed on the extremity and immediately below the joint;

an intermediate member coupled to said first extremity engaging structure and said second extremity engaging structure, so as to permit relative movement therebetween; and said intermediate member being configured with a variable resistance mechanism for resisting relative movement between said first extremity engaging structure and said second extremity engaging structure.

BRIEF DESCRIPTION OF THE DRAWINGS

The invention may be more fully understood by reading the foregoing description of the preferred embodiments of the invention, in conjunction with the appended drawings wherein.

DETAILED DESCRIPTION

Figure 1:
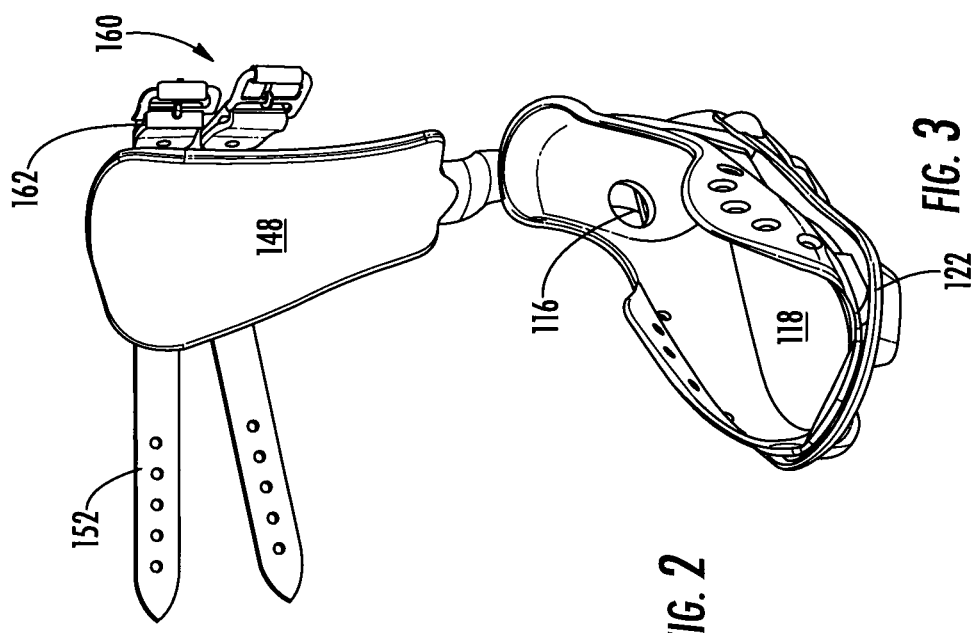
FIG. 1 is a right level rear end perspective view of the system of the present invention.
Figure 2:
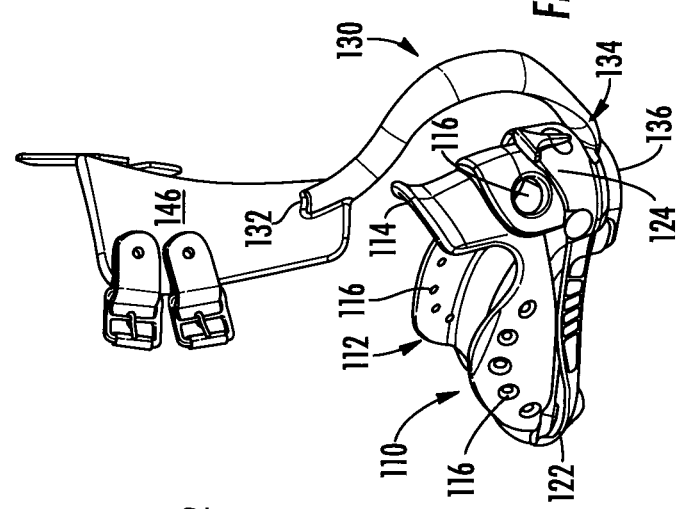
FIG. 2 is a left rear end perspective view of the system of the present invention from a raised vantage point with respect to FIG. 1.
Figure 3:
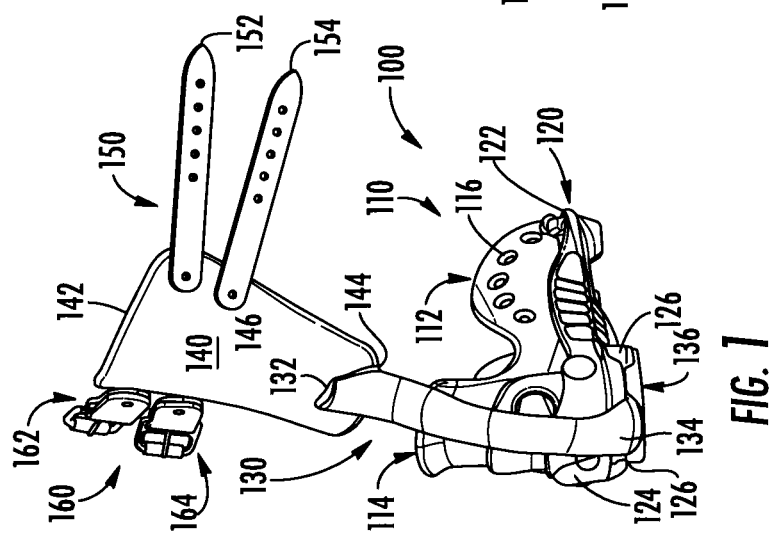
FIG. 3 is a left front end perspective view of the system of the present invention from an alternate vantage point with respect to FIG. 1.
Figure 4:
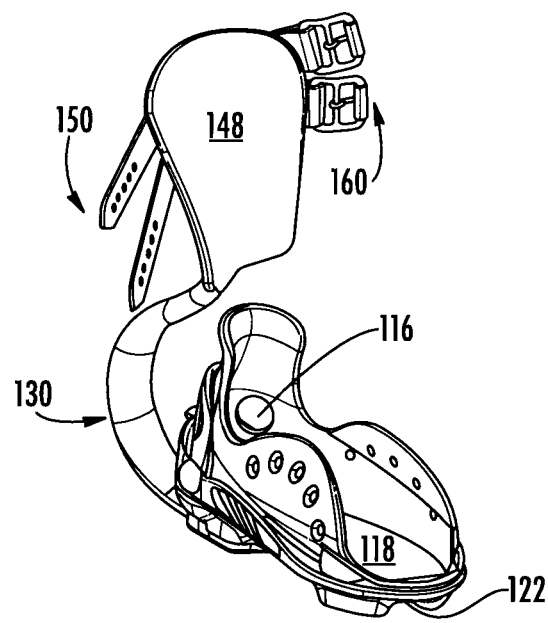
FIG. 4 is a right front end perspective view of the system of the present invention from an alternate vantage point with respect to FIG. 1.
Figure 5:
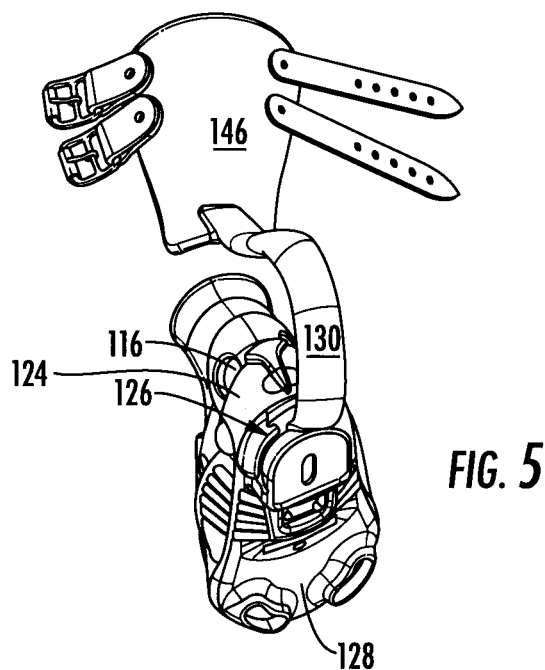
FIG. 5 is a left rear end perspective view of the system of the present invention from a lowered vantage point with respect to FIG. 1.

Although described with particular reference to the Ponseti method for treating clubfoot, some embodiments of the method and apparatus of the present invention could be unrelated to the Ponseti method. The examples shown of shoes use children sized shoes because the Ponseti method is used overwhelmingly on children; however, adult use of orthoses, as described and claimed herein, could be readily accomplished with minor adaptations without departing from the spirit and scope of the present invention. Also, while a bar-less brace, such as shown in US Patent Application 2013/0226059 A1 to Phillip G. L. Morris, is discussed; it should be understood that some embodiments of the present invention could relate to braces which are not bar-less. Additionally, while some aspects of the present invention relate to a flexible brace; the system and method of the present invention can be implemented in many different types of devices which may not be flexible.

In an embodiment, the present invention is a system and method for solving foot and gait problems. The details below should be viewed as examples of many potential variations of the present invention which are protected hereunder.

Now referring to FIGS. 1-5, there are shown various views of the present invention generally described as flexible bar-less brace 100, which has a foot engaging liner 110, a shoe portion 120, calf to heel connection structure 130, calf contactor 140, calf straps 150, calf strap buckles 160, each of which is described in more detail below. Many portions of the present invention are similar to products made in the past and commercially available from MD Orthopaedics of Wayland, Iowa found at www.mdorthopaedics.com.

Foot engaging liner 110 is the portion of the system which contacts the foot or stocking of the patient. It is shown having a foot engaging liner upper 112, which forms a side to cushion the patient's foot from the upper strapping portion, not shown, but well known in the art. Foot engaging liner 110 contains foot engaging liner heel portion 114, liner orifices 116, and foot engaging liner sole portion 118. Shoe portion 120 provides substantial, if not rigid, support of the foot from below, with the aid of shoe bottom portion 128. Shoe toe portion 122 and opposing end shoe heel portion 124 are also shown. Shoe slot forming bottom portion 126 is formed in shoe portion 120 to detachably accept an elongated member. This slot and attachment to the elongated member are similar, sometimes identical and interchangeable with prior shoes from MD Orthopaedics, whoever in the past the elongated member has generally been a substantially horizontal Denis Browne splint used in the Ponseti method of correcting club feet. The present invention allows for the many existing shoes from MD Orthopaedics to be reused with a completely different brace to solve problems beyond those solved with the Denis Browne splint.

Calf to heel connection structure 130 is coupled, at the calf to heel bottom side 134, to the shoe slot forming bottom portion 126, but it extends from or is curved to extend from the point of attachment to shoe slot forming bottom portion 126 in a generally vertical and upward direction to calf to heel top side 132. FIGS. 1-5 show a substantially C shaped arched or curved portion of calf to heel connection structures 130 with an open side generally pointing in a direction parallel with a line drawn from a heel of the shoe to the toe of the shoe. This may be a preferred arrangement for some patients but other patients may require custom formation of calf to heel connection structure 130. The purpose of calf to heel connection structure 130 is often to apply a pre-biased force on the shoe portion 120 and thereby cause the patients foot to be urged in a predetermined direction for therapeutic treatment of various foot, ankle and gait problems. Depending upon the problem to be corrected, the calf to heel connection structure 130 is twisted in a particular shape and direction to result in the desired direction and magnitude of pre-biasing force on the shoe portion 120. The materials for calf to heel connection structure 130 may be nylon, thermoplastics, and other suitably flexible material and may be constructed using a process such as injection molding, 3D printing, extruding, carving or other suitable processes. Entirely different materials and processes could be substituted, especially if they provide for the ability to change, in a predetermined manner, amount and/or direction, an orientation of a foot when all contact with the ground is ended. In some applications, the calf to heel connection structures 130 could be made to extend generally from the heel of the shoe as is shown in FIGS. 1-7. However, it should be understood that the calf to heel connection structures 130 could be made to connect to the shoe at some point between the heel and the toe, or even at the toe.

Calf to heel top side 132 is coupled to calf contactor 140, which is shown having a calf contactor top side 142, calf contactor bottom side 144, a calf contactor back side 146, and a calf contactor front side 148. Calf contactor 140 is held in place on the patient's leg with calf straps 150, with calf strap 152 and calf strap 154, and calf strap buckles 160 with calf strap buckle 162.

In operation, when the calf contactor 140 is coupled firmly to the patient's leg, and the patient's foot is not in the foot engaging liner 110, the calf to heel connection structure 130 will need to be flexed or stressed with a temporary force, in a direction generally opposite the direction of the pre-biasing force so that the foot will enter easily and be secured in the foot engaging liner 110. When the patient's foot is secured firmly in the foot engaging liner 110, and the temporary force on the calf to heel connection structure 130 is discontinued, the pre-biased force will be acting upon the patient. For example, the pre-biased force would be an upward force on the toe of the shoe if the person suffered from a foot that dropped while walking. The pre-biased force would then tend to elevate the toe when the foot was lifted during walking. Numerous other foot problems could be addressed with different shapes and stresses on the different calf to heel connection structures 130 specially made for the patient's problem. However, for some patients, the calf to heel connection structure 130 could be made to be rigid depending upon the patient's needs.

Figure 6:
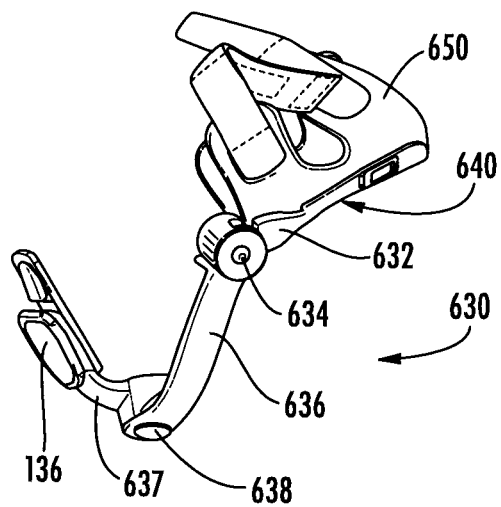
FIG. 6 is a perspective view of an alternate system of the present invention without a shoe attached.
Figure 7:
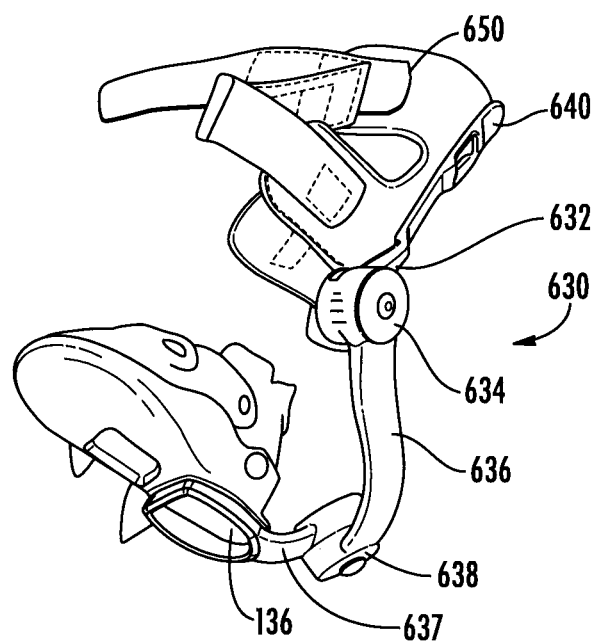
FIG. 7 is a perspective view of the alternate system of FIG. 6 but with a shoe attached.

Now referring to FIGS. 6 and 7, there is shown an alternate embodiment of the present invention, which has a different calf to heel structure which is generally designated 630, which comprises top section 632 which is hingedly coupled to mid section 636 via threaded member 634. Mid section 636 is hingedly coupled to lower section 637 via threaded member 638. If 638 and 634 are sufficiently tight, there will be no internal movement in the pieces of 630. Lower section 637 is coupled to 136 of FIGS. 1-7. FIG. 7 is the same as FIG. 6, except a detachable shoe similar to that shown in FIGS. 1-5 is attached in FIG. 7. The system has an adjustable angle between the portions 632, 636, and 637 of the components of 630, but it is intended that after adjustment that they be restricted from relative movement. In an alternate configuration, a rigid brace could be made where there is no adjustment mechanism and the three portions, 632, 636, and 637, are all a single rigid element. Still other variations are possible.

Figure 8:
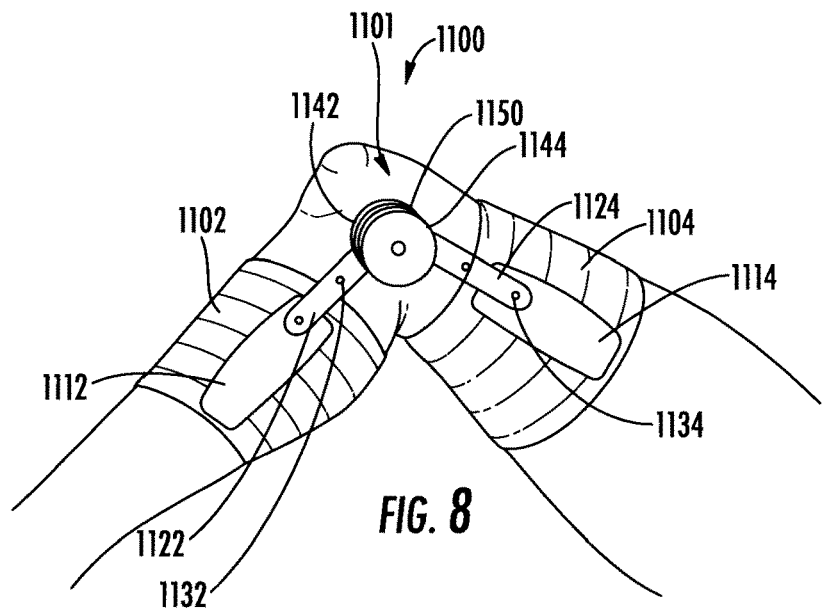
FIG. 8 is a diagram illustrating a simplified knee or elbow orthosis of the present invention.

Now referring to FIG. 8, which shows a diagram illustrating a simplified knee/elbow orthosis 1100 disposed on a human leg or arm with a lower extremity engaging strap 1102 with a lower strap to arm interface 1112 which couples to lower arm 1122 with lower arm fastener hole 1132 therein. A tensioner 1101 made up of lower arm side casing 1142, upper arm side casing 1144, and interchangeable canister 1150 therebetween.

Lower arm 1122 couples to lower arm side casing 1142. Upper extremity engaging strap 1104 is similarly coupled to upper strap to arm interface 1114, to upper arm 1124 which has upper arm fastener hole 1134 therein. Upper arm 1124 is coupled to upper arm side casing 1144.

Knee orthosis, such as shown, can be configured to perform in different ways, depending on whether the orthosis is attempting to provide exercise resistance, make it easier for the patient to stand from a seated position, and other.

Depending on the particular use and the changing strength and weight of the patient, it may be desirable to change the strength of the spring inside the canister.

Numerous methods are well known in the art for changing the strength or force required to store energy in the spring. These methods can include altering the point of attachment of the spring with a member which it interacts. Often adjusting spring tensions can be delicate, require significant strength or skill. In certain situations, a patient may desire an adjustment of the spring but gives up because it is too difficult.

Figure 9:
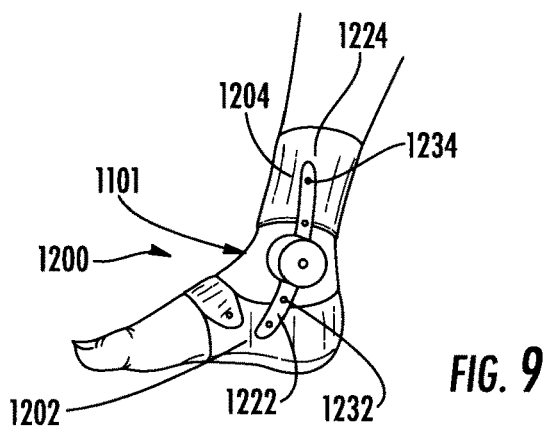
FIG. 9 is a simplified diagram of an ankle orthosis of the present invention.

Now referring to FIG. 9, there is an ankle orthosis, generally designated 1200, which is very similar in form and function to the orthosis 1100 of FIG. 8, except for the interface with the foot and the leg.

More specifically, there is shown a lower extremity engaging shoe 1202 which may include a strap over the top of the foot. Upper extremity engaging strap 1204 may be similar in many ways to lower extremity engaging strap 1102 and upper extremity engaging strap 1104. These two items 1202 and 1204 may be connected with lower arm 1222, which may have a lower arm fastener hole 1232 therein and similar with an upper arm 1224, which may have an upper arm fastener hole 1234 therein. Between the arms 1222 and 1224, the tensioner 1101 may be the same as in FIG. 8.

Figure 10:
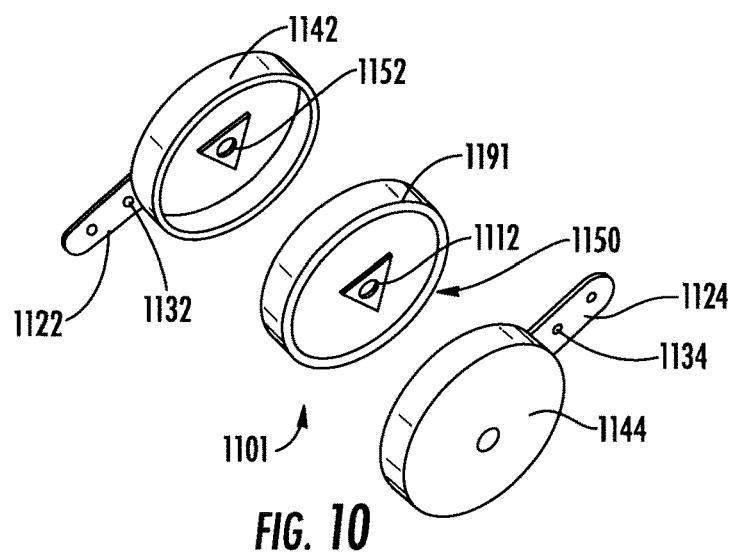
FIG. 10 is a partially exploded view of a force producing apparatus of FIGS. 8 and 9.

Now referring to FIG. 10, there is shown a partially exploded view of the tensioner 1150. Lower arm 1122 is shown combined with lower arm side casing 1142, which has a lower rotation preventing surface feature 1152 which is designed to engage with a feature (not shown) of interchangeable canister 1150, which is shown having a canister outer cylindrical surface 1191 and an upper rotation preventing surface feature 1192, which is designed to mate with a feature (not shown) in upper arm side casing 1144.

In operation, the interchangeable canister 1150 may function as follows: each side engages with a feature in lower arm side casing 1142 and upper arm side casing 1144 and, when rotation occurs, with respect to lower arm 1122 and upper arm 1124, rotation resisting forces within interchangeable canister 1150 are affected.

Figure 11:
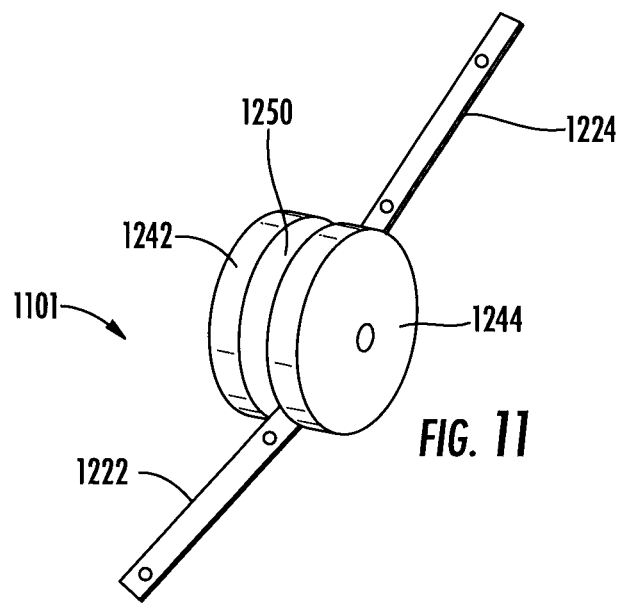
FIG. 11 is an enlarged isolated assembled view of the apparatus of FIG. 10.

Now referring to FIG. 11, there is shown a close up view of the tensioner 1101 with the arms 1222 and 1224 of FIG. 9.

Figure 12:
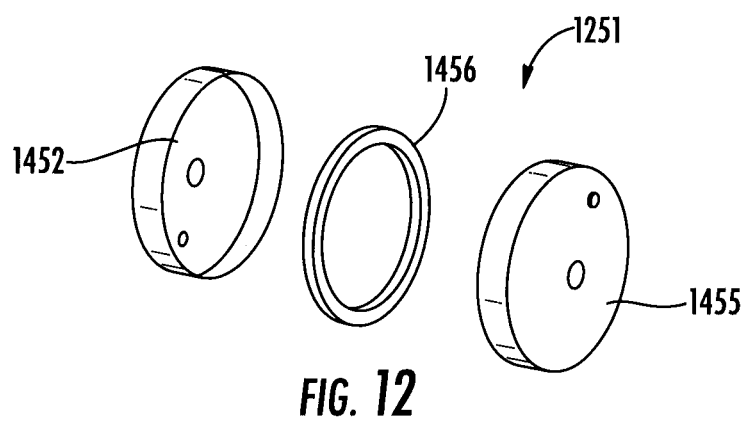
FIG. 12 is an exploded view of a tensioner canister of FIG. 11.

FIG. 12 shows one embodiment 1251 of the canister 1250 (seen in a cap between casing 1242 and 1244 in FIG. 11) where the internal component is a canister spring 1456, which is coupled at each end to holes in either first canister casing 1452 or second canister casing 1455. Rotation of casings 1452 and 1455, with respect to each other, will result in manipulation of the canister spring 1456.

Figure 13:
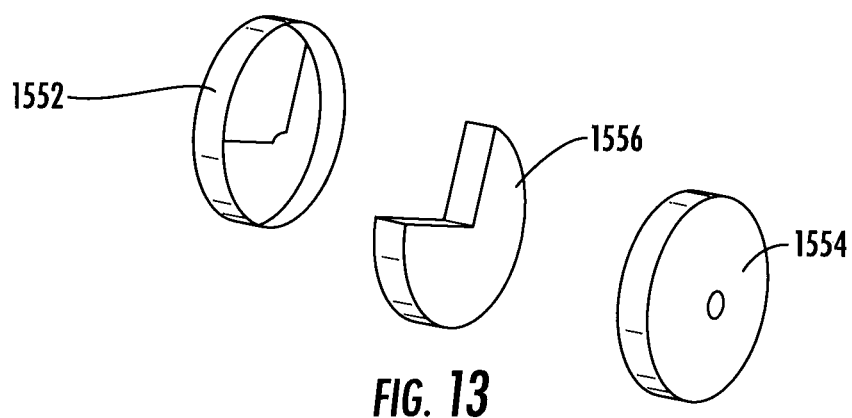
FIG. 13 is an alternate embodiment of a tensioner canister of FIG. 11.
Figure 13A:
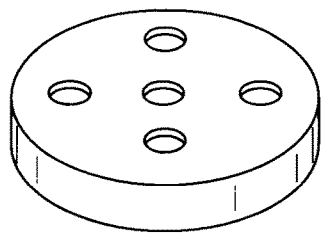
FIGS. 13A-13F are alternate embodiments of a portion of the tensioner canister of FIG. 13.
Figure 13B:
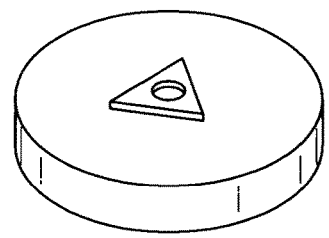
Figure 13C:
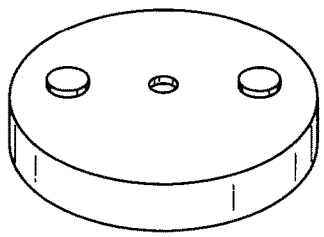
Figure 13D:
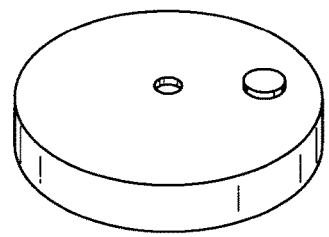
Figure 13E:
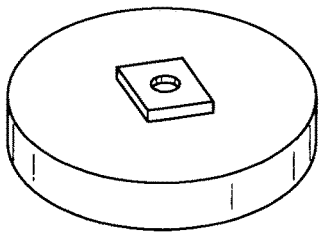
Figure 13F:
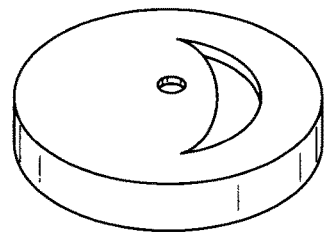

Now referring to FIG. 13, there is shown an alternate embodiment 1252 of the canister 1250, which includes a first matter engaging casing 1552, a second casing 1554 and compressible matter 1556 disposed therebetween. Not shown in the figures, but included in the present invention, is some feature for transferring motion from upper arm side casing 1244 to second casing 1554, as well as some feature from transferring rotational motion from second casing 1554 to compressible matter 1556. There is shown a mating region in first matter engaging casing 1552, which mates with portions of compressible matter 1556 so that rotation of first matter engaging casing 1552, with respect to second casing 1554, results in either compression or expansion of compressible matter 1556. Compressible matter 1556, which may be a rubbery natural or synthetic material or any suitable material which can be formed and functionally deployed to essentially replace the canister spring 1456 of FIG. 12. Note that the canister spring 1456 may be configured to pull and or push. Without using a very strong adhesive or other connection method, the compressible matter will likely be configure to just push.

Now referring to FIG. 13A-13F, there are alternate embodiments of surface features on lower arm side casing 1242, upper arm side casing 1244, and the sides of the interchangeable canister 1150 and interchangeable canister 1250.

Figure 14:
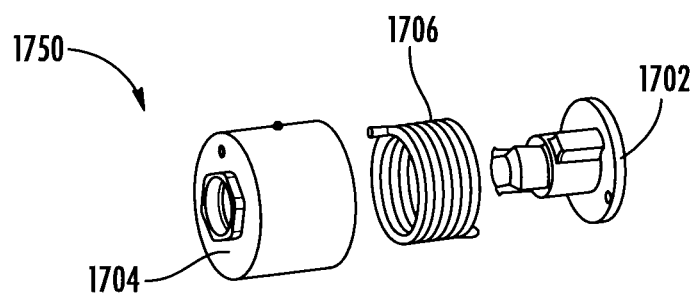
FIG. 14 is an exploded view of yet another alternate embodiment of a canister of the present invention.
Figure 15:
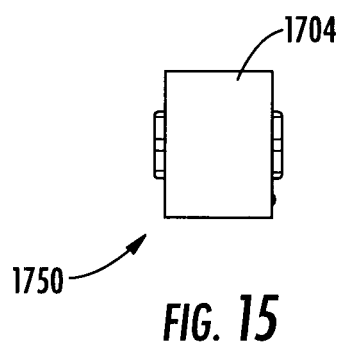
FIG. 15 is a non-exploded view of the canister of FIG. 14.

Now referring to FIG. 14, there is shown another alternate embodiment of the canister generally designated as 1750, which is shown in an exploded view, which includes inner pill 1702, outer pill 1704 and torsion spring 1706. FIG. 15 is an assembled view of canister 1750.

Figure 16:
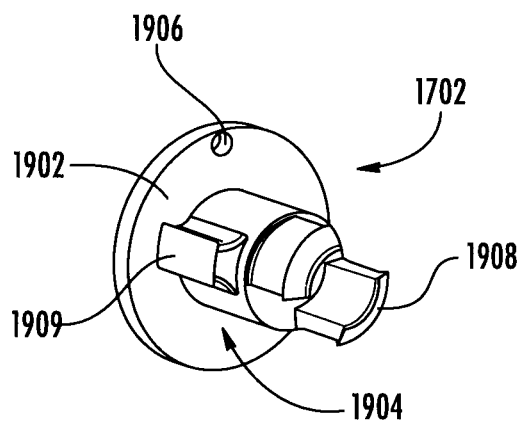
FIG. 16 is a perspective view of a portion of the canister shown in FIGS. 14 and 15.
Figure 17:
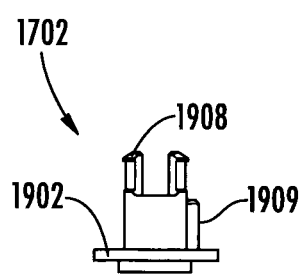
FIG. 17 is a side view of the portion shown in FIG. 16.

Now referring to FIG. 16, there is shown an enlarged perspective view of the inner pill 1702, which includes inner pill flange 1902, with inner pill spring receiving hole 1906 therein, and inner pill core 1904 thereon, which has an inner pill radial extension 1909 attached thereto. Atop inner pill core 1904 is inner pill first tooth 1908. Inner pill 1702 is inserted into outer pill 1704 along with torsion spring 1706. Inner pill flange 1902 forms an end of canister 1750. FIG. 17 shows a side view of inner pill 1702.

Figure 18:
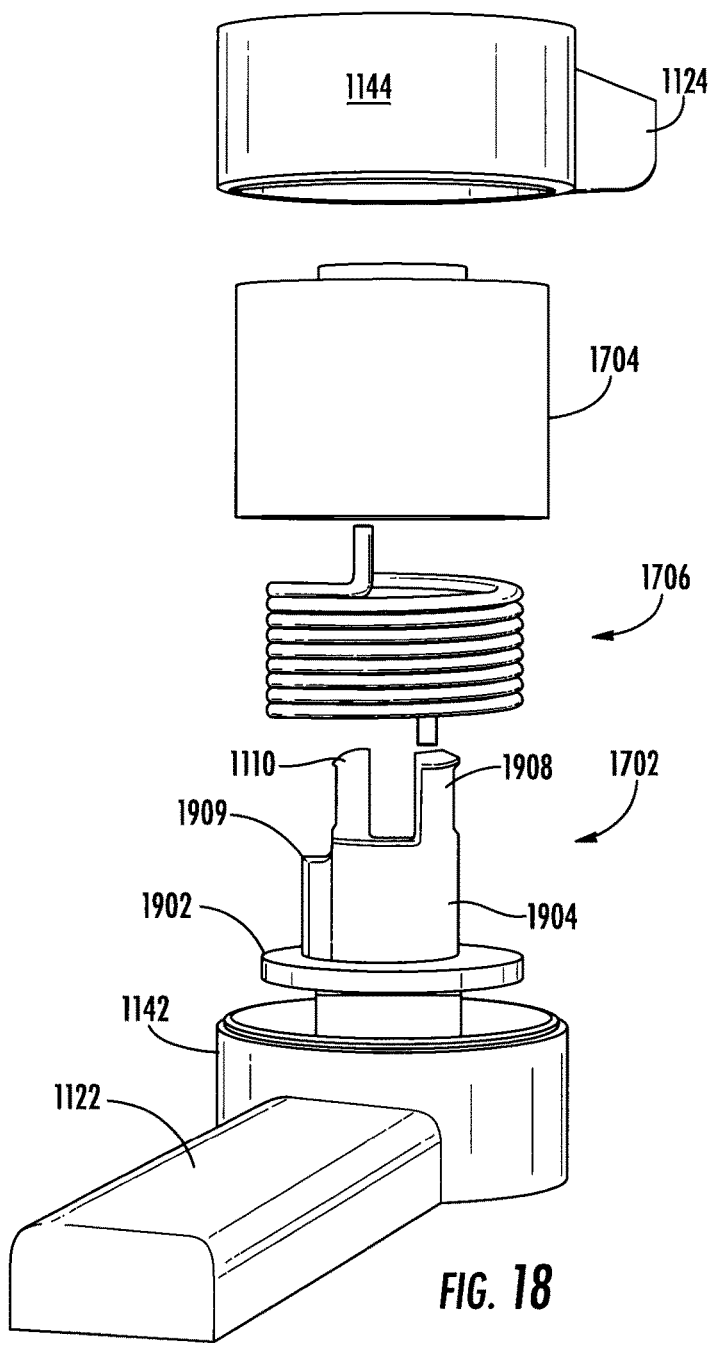
FIG. 18 is an exploded perspective view of an embodiment of the present invention which shows the canister portions shown in FIGS. 14-17.

Now referring to FIG. 18, there is shown an exploded view of the present invention which includes inner pill second tooth 11110.

Figure 19:
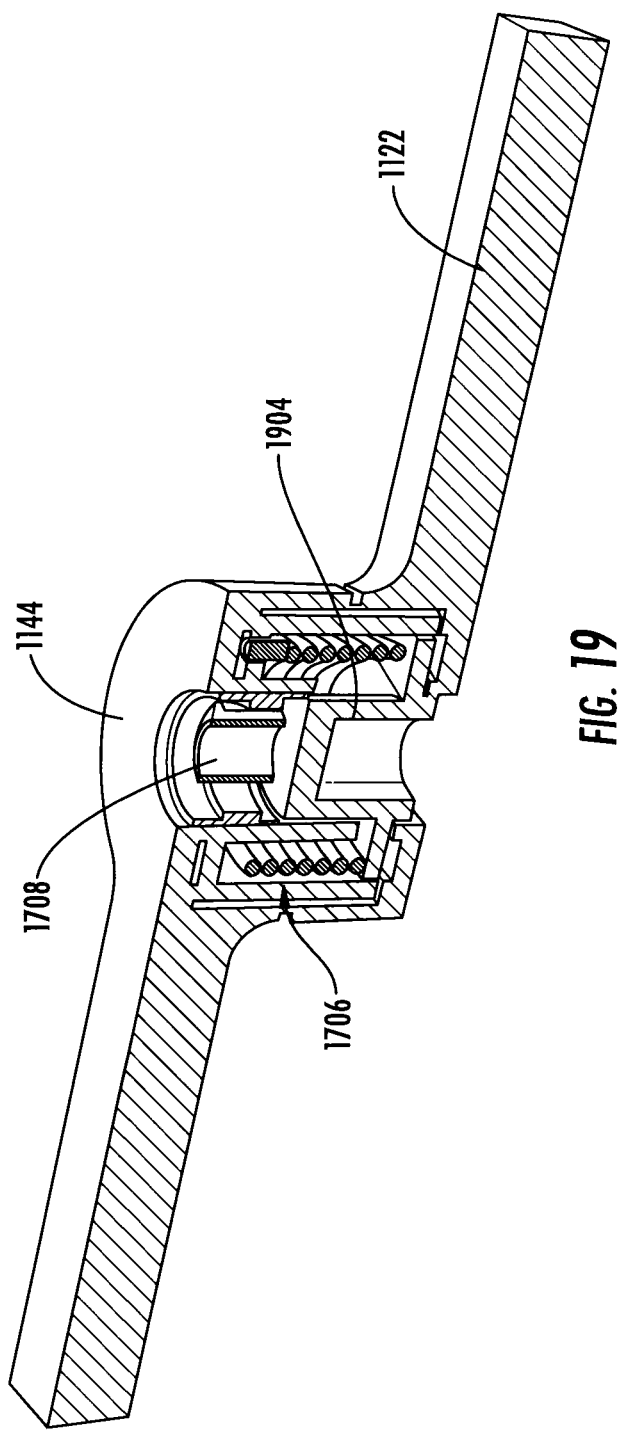
FIG. 19 is perspective view of a bi-section of the assembled apparatus of FIG. 18.

Now referring to FIG. 19, there is shown a perspective bisected view of the system of the present invention.

Figure 20:
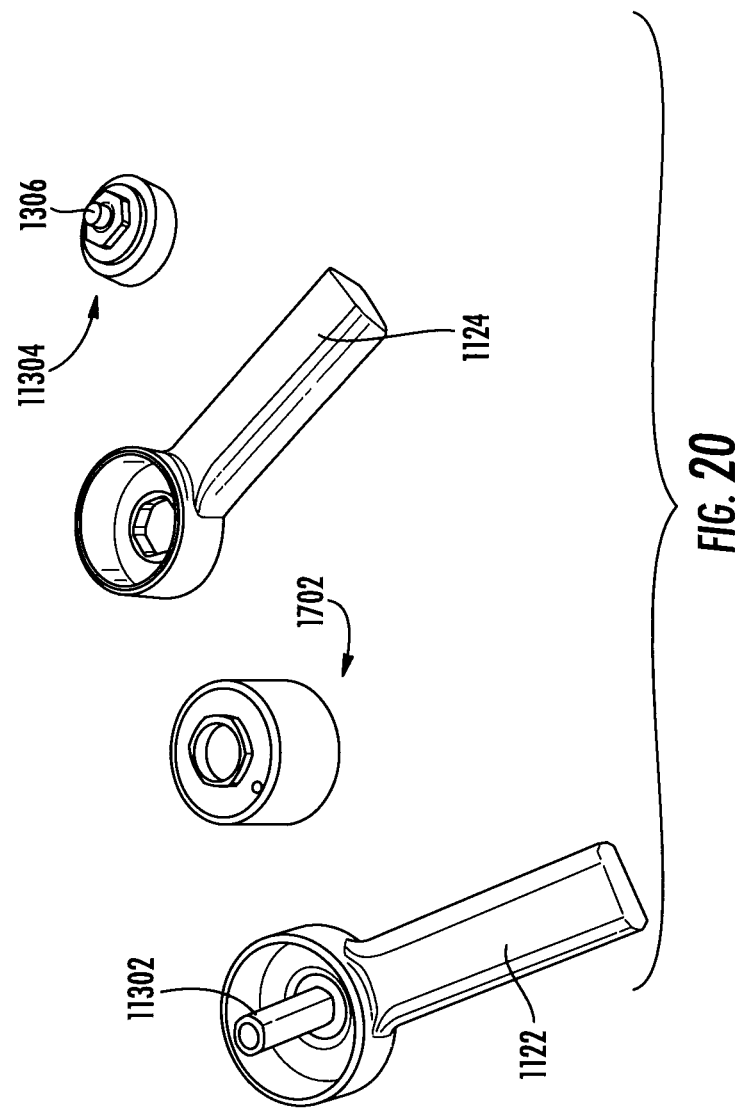
FIG. 20 is an alternate embodiment of the present invention in a disassembled state.

Now referring to FIG. 20, there is shown an alternate variation of the present invention, which includes a side casing central stem 11302, side casing thumb screw 11304 and a thumb screw threaded post 11306.

Figure 21:
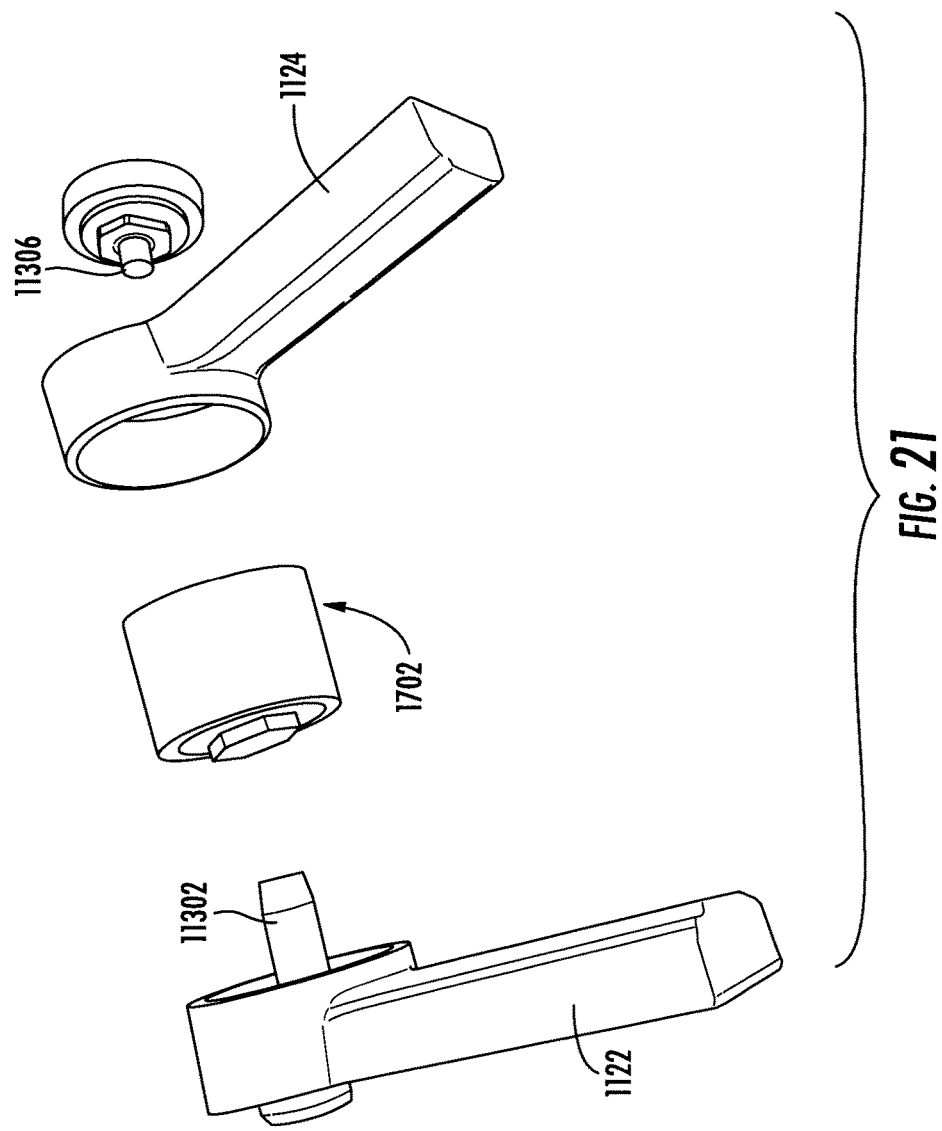
FIG. 21 is an exploded view of the embodiment of the apparatus of FIG. 20.
Figure 22:
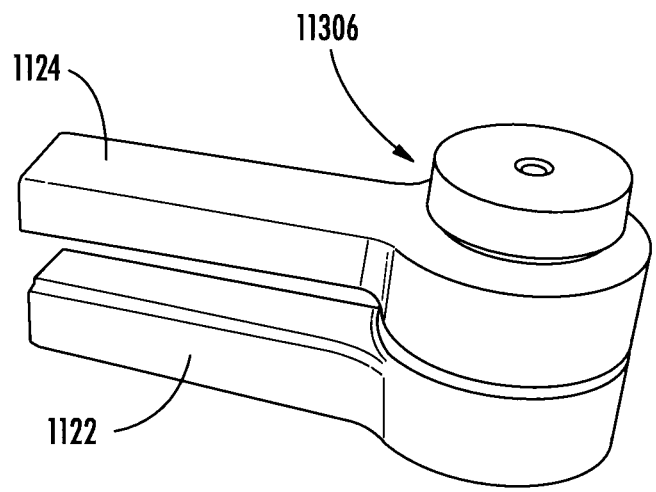
FIG. 22 is an assembled view of the embodiment of FIG. 21.

FIG. 21 shows an exploded view while FIG. 22 shows a fully assembled view.

Now referring to FIG. 22, there is shown an assembled view of the embodiment of FIG. 21.

Figure 23:
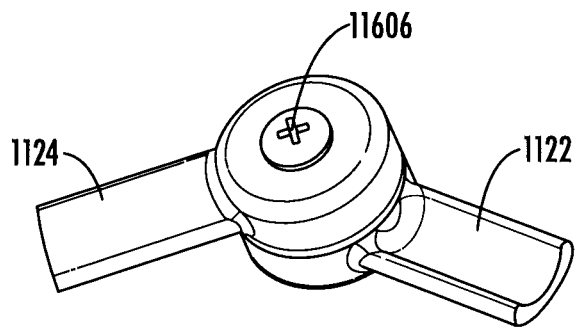
FIG. 23 is an assembled view of an alternate embodiment of the present invention.

Now referring to FIG. 23, there is shown an alternate embodiment of the present invention which is very similar to the embodiment of FIG. 20 except that the thumb screw 11306 of FIG. 20 is replaced with a Philips head screw 11606.

Figure 24:
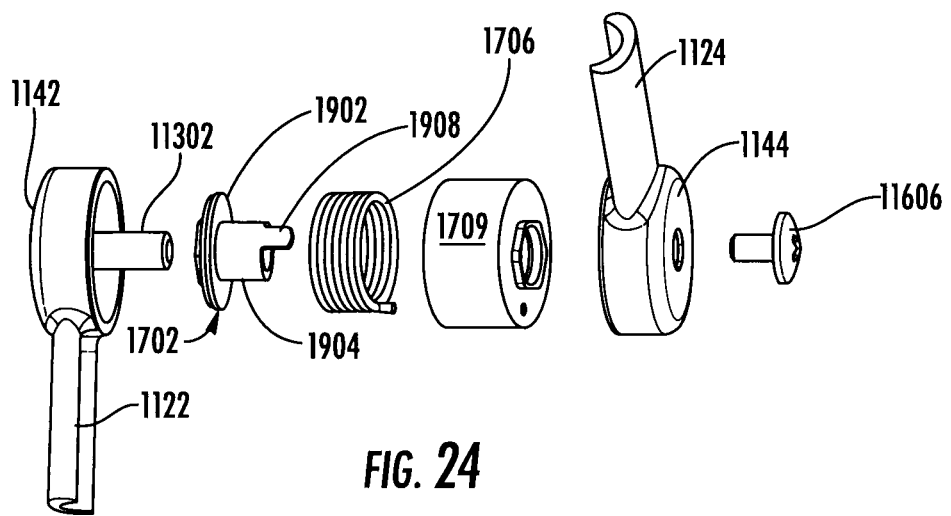
FIG. 24 is an exploded view of the embodiment of FIG. 23.

Now referring to FIG. 24, there is shown an exploded view of the embodiment of FIG. 23.

Figure 25:
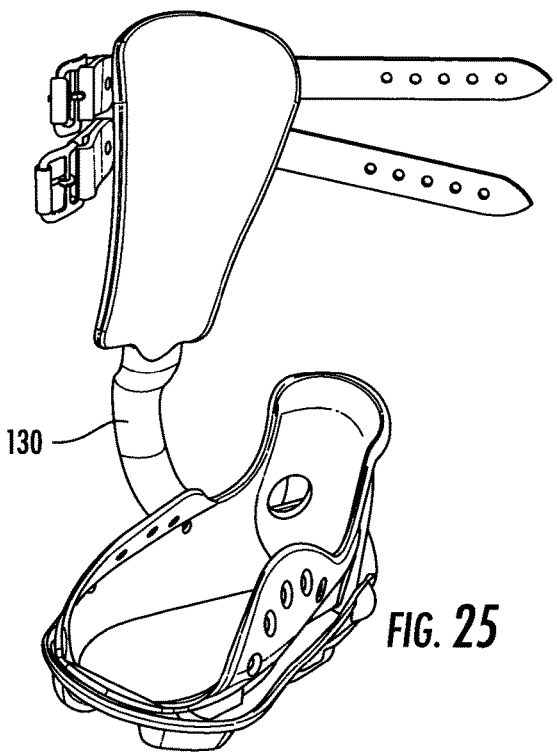
FIG. 25 is a frontal perspective view of an alternate side attached embodiment of the present invention from above.
Figure 26:
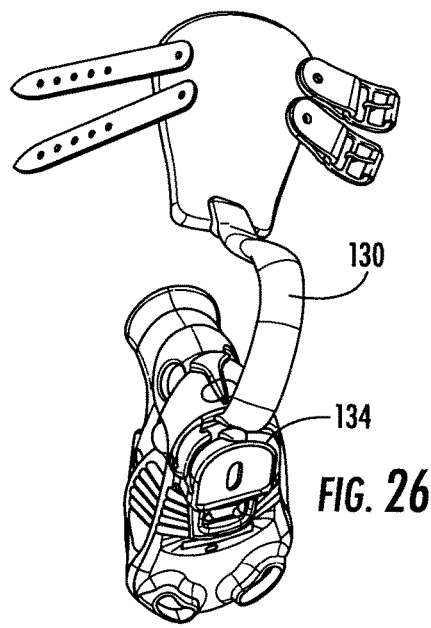
FIG. 26 is a rear perspective view of the embodiment of FIG. 25 from below.
Figure 27:
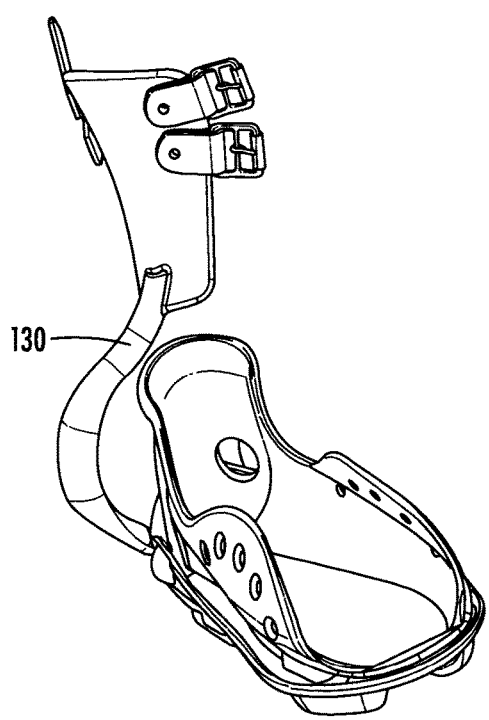
FIG. 27 is an alternate side view of the embodiment of FIG. 25 from another side.

Now referring to FIGS. 25-27, there is shown an alternate embodiment of the present invention where the calf to heel connection structure 130 is formed in a different shape with a different curvature and attached at a different and more lateral location. Other details could be the same as the embodiment of FIGS. 1-5.

Figure 30:
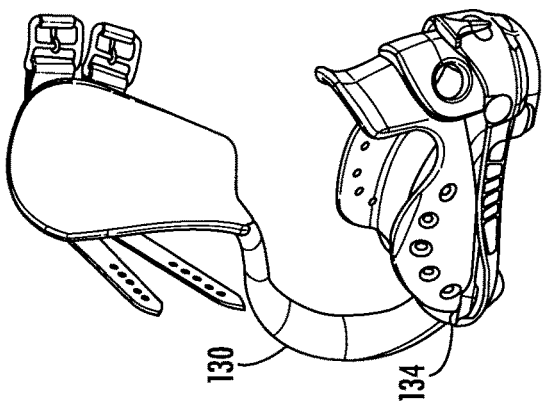
FIG. 30 is a rear view of the embodiment of FIG. 29.
Figure 29:
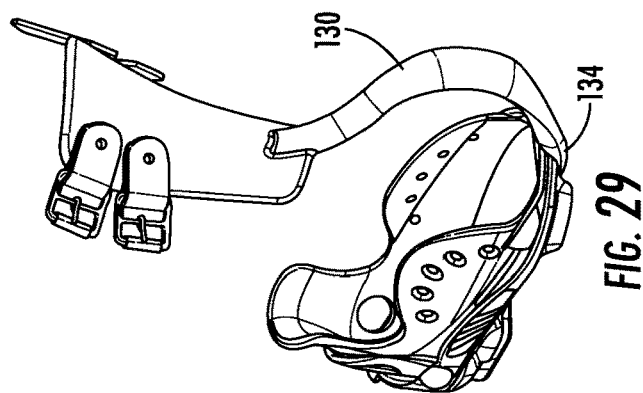
FIG. 29 is a frontal view of the embodiment of FIG. 28.
Figure 28:
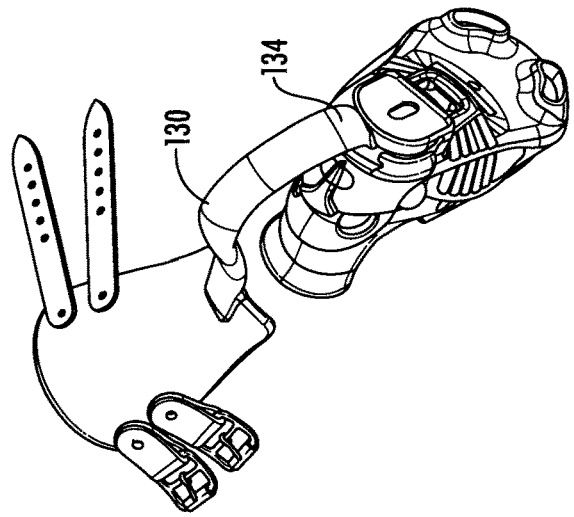
FIG. 28 is an alternate front attached embodiment of the present invention from below.

Now referring to FIGS. 28-30, there is shown an alternate embodiment of the present invention where the calf to heel connection structure 130 is formed in a different shape with a different curvature and attached at a different and more frontal location. Other details could be the same as the embodiment of FIGS. 1-5. The precise implementation of the present invention will vary depending upon the particular application.

It is thought that the method and apparatus of the present invention will be understood from the foregoing description and that it will be apparent that various changes may be made in the form, construct steps and arrangement of the parts and steps thereof without departing from the spirit and scope of the invention or sacrificing all of their material advantages. The form herein described is merely a preferred exemplary embodiment thereof.

We claim:

1. An orthosis for use in treating clubfoot, the orthosis comprising, in operative combination:
   a first extremity engaging structure configured to be disposed on an extremity and immediately above a joint on the extremity;
   a second extremity engaging structure configured to be disposed on the extremity and immediately below the joint;
   a hinge coupled to said first extremity engaging structure and said second extremity engaging structure;
   said hinge being configured with a variable resistance mechanism for resisting relative movement between said first extremity engaging structure and said second extremity engaging structure; and
   a first canister, disposed in said hinge, and having a first predetermined resistance characteristic and a first predetermined exterior shape and size characteristic,
   wherein said first canister has a first canister exterior shape which permits insertion of said first canister into a first side casing and mating of said first canister with said first side casing,
   wherein said first canister exterior shape includes a first rotation preventing surface feature and said first rotation preventing surface feature is triangularly shaped.

2. The orthosis of claim 1 further comprising a first compressible structure disposed in said first canister where said first compressible structure provides a predetermined characteristic for resisting movement of said hinge.

3. The orthosis of claim 2 wherein said first compressible structure is a spring.

4. The orthosis of claim 1 wherein the orthosis is configured to be disposed on a leg having a knee with the first extremity engaging structure configured to be disposed immediately above the knee on the leg and the second extremity engaging structure configured to be disposed immediately below the knee on the leg.

5. The orthosis of claim 1 wherein the orthosis is configured to be disposed on an arm having an elbow with the first extremity engaging structure configured to be disposed immediately above the elbow on the arm and the second extremity engaging structure configured to be disposed immediately below the elbow on the arm.

6. The orthosis of claim 1 wherein a first hinge portion of said hinge is directly coupled to said first extremity engaging structure and a second hinge portion of said hinge is directly coupled to said second extremity engaging structure.

7. The orthosis of claim 1 wherein said first canister is one of a plurality of interchangeable canisters which are functionally identical except for having different characteristics for resisting movement of the hinges.

8. An orthosis for use in treating clubfoot, the orthosis comprising, in operative combination:
   a first extremity engaging structure configured to be disposed on an extremity and immediately above a joint on the extremity;
   a second extremity engaging structure configured to be disposed on the extremity and immediately below the joint;
   an intermediate structure coupled to said first extremity engaging structure and said second extremity engaging structure, so as to permit relative movement therebetween; and
   said intermediate structure being configured with a variable resistance characteristic for resisting relative movement between said first extremity engaging structure and said second extremity engaging structure,
   wherein said intermediate structure is an articulated rigid arm with a hinge therein, where the hinge is configured to receive a series of a plurality of interchangeable spring canisters where each of said plurality of interchangeable spring canisters is functionally identical except for differing spring configurations which produce a predetermined difference in spring constant to match with predetermined different therapeutic needs for resistance in the articulated rigid arm, and
   wherein each canister of said plurality of interchangeable spring canisters has a canister exterior shape which permits insertion of said canister into a first side casing and mating of said canister with said first side casing,
   wherein said canister exterior shape includes a first rotation preventing surface feature and said first rotation preventing surface feature is triangularly shaped.

9. The orthosis of claim 8 where said first extremity engaging structure is a padded calf engaging structure.

10. The orthosis of claim 9 where said second extremity engaging structure is a pre-existing commercially available foot orthosis, and said intermediate structure is coupled directly to said pre-existing commercially available foot orthosis by a known shoe quick connect mechanism.

11. The orthosis of claim 10 wherein said intermediate structure is a single curved flexible member.

* * * * *